(12) United States Patent
Wills et al.

(10) Patent No.: US 10,299,901 B2
(45) Date of Patent: May 28, 2019

(54) DRIVE SYSTEM FOR PERSONAL-CARE APPLIANCE AND METHOD OF OPERATION THEREOF

(71) Applicant: KONINKLIJKE PHILIPS N.V., Eindhoven (NL)

(72) Inventors: Scott Robert Wills, Shoreline, WA (US); Alexandra Kulas, Sammamish, WA (US); Franciscus Jozef Bosman, Drachten (NL); Pieter Johannes Bax, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 325 days.

(21) Appl. No.: 15/316,889

(22) PCT Filed: May 19, 2015

(86) PCT No.: PCT/IB2015/053681
§ 371 (c)(1),
(2) Date: Dec. 7, 2016

(87) PCT Pub. No.: WO2015/193752
PCT Pub. Date: Dec. 23, 2015

(65) Prior Publication Data
US 2017/0100224 A1 Apr. 13, 2017

Related U.S. Application Data

(60) Provisional application No. 62/013,052, filed on Jun. 17, 2014.

(51) Int. Cl.
*H02K 33/00* (2006.01)
*A61C 17/34* (2006.01)
(Continued)

(52) U.S. Cl.
CPC .......... *A61C 17/3472* (2013.01); *A46B 9/04* (2013.01); *A61C 15/047* (2013.01); *A61C 17/22* (2013.01);
(Continued)

(58) Field of Classification Search
CPC ........ H02K 33/00; H02K 33/02; H02K 33/04; A61C 17/3445; A61C 17/3418
See application file for complete search history.

(56) References Cited

U.S. PATENT DOCUMENTS 4,420,851 A   12/1983   Wiener
5,263,218 A * 11/1993  Giuliani ................ A61C 17/20
                                                         15/22.1
(Continued)

FOREIGN PATENT DOCUMENTS

CN   2451073 Y   10/2001
EP   0163819 A2  12/1985
(Continued)

*Primary Examiner* — Dang D Le

(57) ABSTRACT

A power toothbrush apparatus may include a body having a cavity and an opening leading to the cavity. An electric motor may be situated within the cavity and may include first and second biasing members; a stator casing situated between, and linearly biased by, the first and second biasing members, the stator casing may further include at least one opening and at least one electromagnet to generate a magnetic field; and a rotor which may have opposed ends and which may extend through the at least one opening of the stator casing, the rotor may further include an output shaft. The power toothbrush may further include a workpiece having a brush head coupled thereto and which may be coupled to one of the opposed ends of the output shaft.

6 Claims, 7 Drawing Sheets

(51) Int. Cl.
*A61C 15/04* (2006.01)
*A61C 17/22* (2006.01)
*A46B 9/04* (2006.01)
*H02K 33/16* (2006.01)

(52) U.S. Cl.
CPC ........ *A61C 17/221* (2013.01); *A61C 17/3418* (2013.01); *A61C 17/3445* (2013.01); *H02K 33/16* (2013.01); *H02K 2201/18* (2013.01)

(56) References Cited

U.S. PATENT DOCUMENTS

| | | | |
|---|---|---|---|
| 6,691,363 | B2 | 2/2004 | Huen |
| 7,315,098 | B2 * | 1/2008 | Kunita ............... A61C 17/3445 |
| | | | 15/22.1 |
| 7,328,474 | B2 * | 2/2008 | Nishinaka .......... A61C 17/3445 |
| | | | 15/22.1 |
| 7,443,059 | B2 | 10/2008 | Kobayashi et al. |
| 7,960,877 | B2 * | 6/2011 | Luo .................... A61C 17/3418 |
| | | | 15/22.1 |
| 2004/0010871 | A1 | 1/2004 | Nishinaka et al. |
| 2005/0235438 | A1 * | 10/2005 | Motohashi ......... A61C 17/3472 |
| | | | 15/22.1 |
| 2006/0158048 | A1 | 7/2006 | Kobayashi et al. |
| 2006/0168745 | A1 * | 8/2006 | Kobayashi ......... A61C 17/3445 |
| | | | 15/22.1 |
| 2008/0258566 | A1 * | 10/2008 | Shimizu ............. A61C 17/3445 |
| | | | 310/12.04 |
| 2010/0154151 | A1 | 6/2010 | Grez et al. |
| 2011/0239383 | A1 * | 10/2011 | Nishiura ............ A61C 17/3445 |
| | | | 15/22.1 |

FOREIGN PATENT DOCUMENTS

| | | |
|---|---|---|
| EP | 1348400 A1 | 10/2003 |
| EP | 1638193 A1 | 3/2006 |
| EP | 1684401 A1 | 7/2006 |
| EP | 1935371 A1 | 6/2008 |
| JP | 2002199689 A | 7/2002 |
| WO | 2004047670 | 6/2004 |
| WO | 2005046507 | 5/2005 |

* cited by examiner

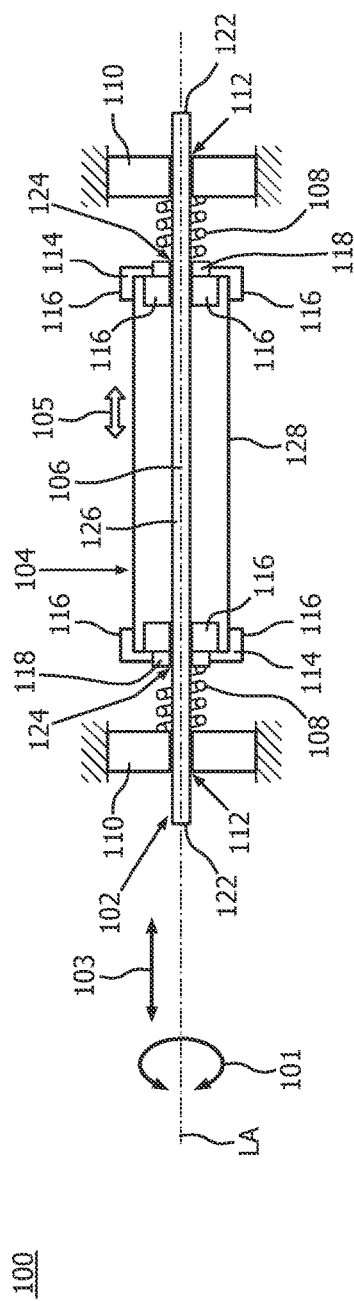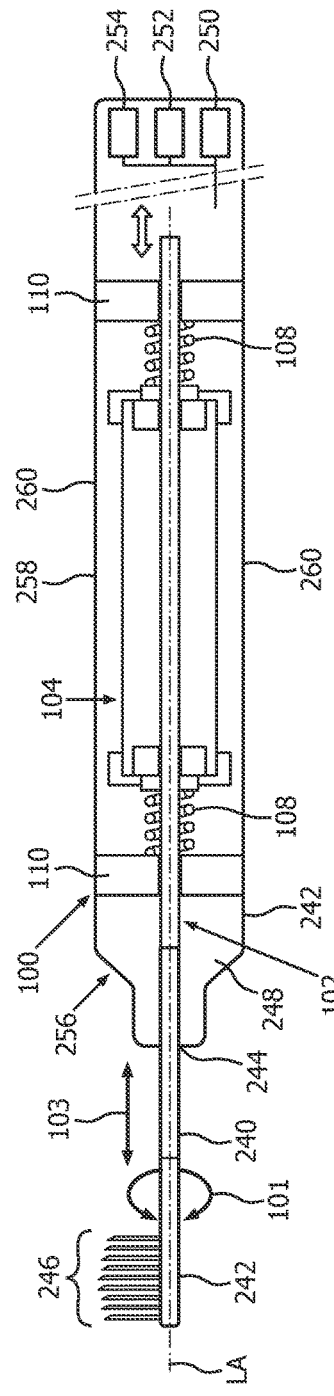

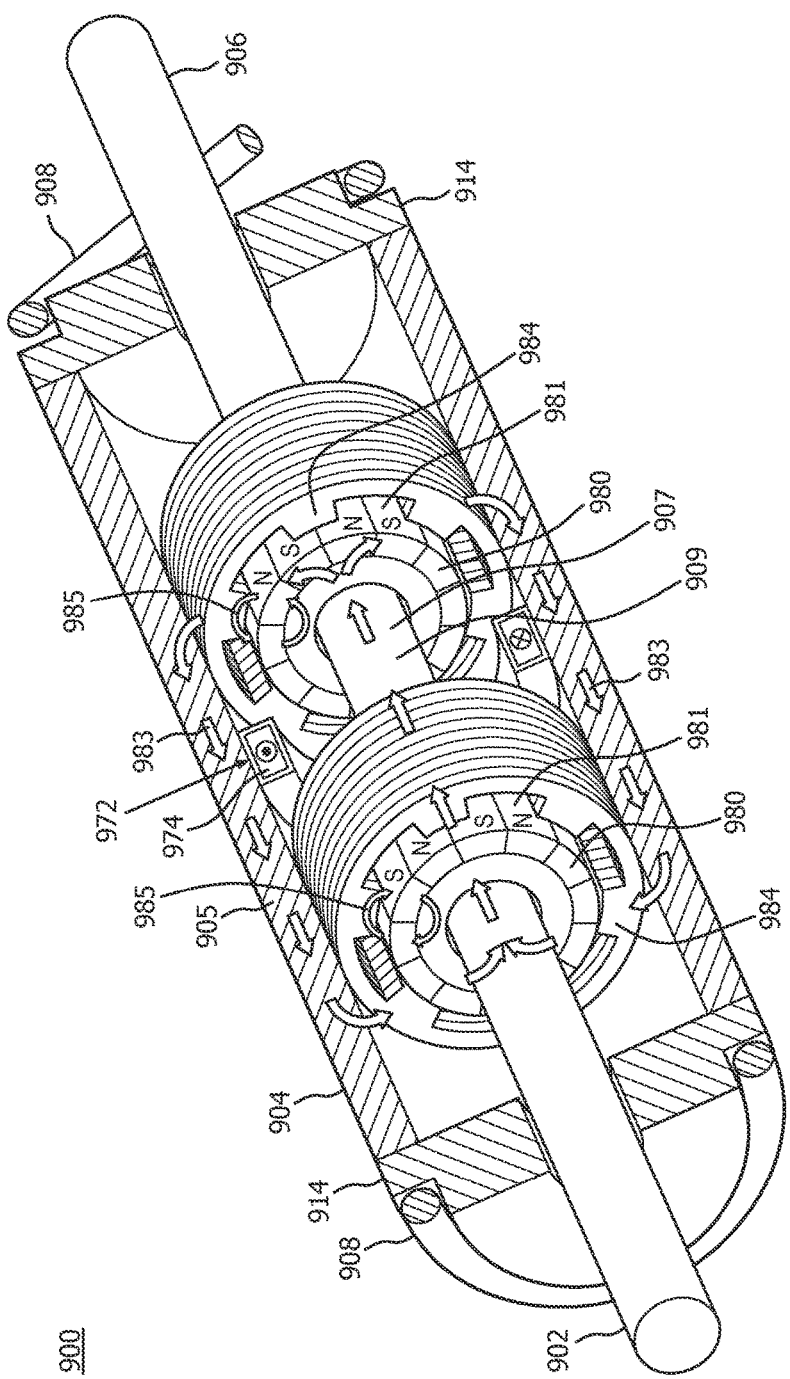

DRIVE SYSTEM FOR PERSONAL-CARE APPLIANCE AND METHOD OF OPERATION THEREOF

CROSS-REFERENCE TO PRIOR APPLICATIONS

This application is the U.S. National Phase application under 35 U.S.C. § 371 of International Application No. PCT/IB2015/053681, filed on May 19, 2015, which claims the benefit of U.S. Provisional Patent Application No. 62/013,052, filed on Jun. 17, 2014. These applications are hereby incorporated by reference herein.

The present system relates to a drive system for a personal care appliance (PCA) such as an automatic toothbrush and, more particularly, to a resonant high-frequency drive system with active vibration dampening to reduce linear and rotational vibration in a personal care appliance such as an automatic toothbrush or the like and a method of operation thereof.

Resonant high-frequency electronic personal care appliances, such as automatic toothbrushes, are commonly used by consumers for personal care. These devices typically operate at high frequencies which often exceed 100 Hz and are used to operate various cleaning devices such as a brush head. Although high-frequency brushing action of the brush head is desirable to remove debris and plaque, the high-frequency brushing action can cause vibration which is transferred to a handle of the toothbrush during use. This vibration is undesirable as it can result in user discomfort.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed a power toothbrush apparatus, which may include a body defining a cavity and an opening; an electric motor situated within the cavity which may include, first and second biasing members, a stator casing situated between and linearly biased by the first and second biasing members, the stator casing may include an opening and at least one electromagnet to generate a magnetic field, and/or a rotor having opposed ends and extending through the stator casing, the rotor may include an output shaft; and/or a workpiece which may include a brush head at one end thereof and may be coupled to one of the opposed ends of the output shaft.

It is also envisioned that each of the first and second biasing members may have opposed first and second ends, each of first ends may be fixedly attached to the body and each of the second ends may be adjacent to the stator casing. It is also envisioned that the first and second biasing members may further rotationally bias the stator casing. It is further envisioned that the rotor may further include at least one magnet which interacts with the magnetic field of the at least one electromagnet to reciprocally drive the rotor and the stator casing linearly and rotationally out of phase with each other. In accordance with yet other embodiments of the present system, the apparatus may further include a controller which applies at least one drive signal to the at least one electromagnet to reciprocally drive the stator casing rotationally substantially at a rotational resonant frequency of the stator casing and linearly substantially at a linear resonant frequency of the stator casing. For the sake of clarity and without limitation, it will be assumed that the rotational resonance frequency of the stator casing and the linear resonance frequency of the stator casing substantially correspond with corresponding rotational and linear resonance frequencies for the spring-mass system of the electric motor. However, in accordance with some embodiments, the stator resonance frequencies do not necessarily have to correspond with the rotor resonance frequencies. For example, in these embodiments, in order to achieve a desired amount of vibration attenuation, the stator resonance frequency (e.g., linear or rotational) should be much lower than the corresponding rotor resonance frequency in use. Having the stator resonant frequency (e.g., linear or rotational) near that of the corresponding rotor resonance frequency may prevent vibration attenuation as this may limit the out-of-phase rotor/stator motion upon which the vibration attenuation depends. It is further envisioned that the stator casing is supported by the rotor. Moreover, in accordance with some embodiments, the first and second biasing members may further rotationally bias the stator casing.

In accordance with yet other embodiments of the present system, there is provided a personal care apparatus, which may include a body defining a cavity and an opening; an electric motor situated within the cavity of the body and may include: first and second biasing members, a rotor extending through at least one of the first and second biasing members and may include output shaft having opposed first and second ends, and a stator casing which rotationally and linearly reciprocates relative the body to dampen vibration of electric motor, the stator casing having at first and second ends and at least one electromagnet situated between the first and second ends and configured to output an magnetic field which interacts with the rotor to reciprocally drive the output shaft linearly and rotationally; and/or a workpiece including a brush head coupled to one of the opposed ends of the output shaft.

It is also envisioned that each of the first and second biasing members may be situated between the body and the stator casing and may be fixedly attached at one end to the body portion. It is also envisioned that the first and second biasing members may further rotationally bias the stator casing. It is further envisioned that the rotor may further include at least one magnet which interacts with the magnetic field of the at least one electromagnet to reciprocally drive the rotor and the damper linearly and rotationally out of phase with each other.

It is also envisioned that in some embodiments the output shaft may extend through and support the stator casing. It is also envisioned that the apparatus may include a controller which may generate at least one drive signal to drive the stator casing rotationally at a rotational resonant frequency of the stator casing and linearly at a linear resonant frequency of the stator casing. It is also envisioned that the stator casing may have a resonant frequency which may be substantially the same as a resonant frequency of the rotor.

In accordance with yet further embodiments of the present system, there is provided a personal care apparatus with active vibration dampening. The personal care apparatus may include: a body defining a cavity and an opening; first and second bearings fixedly situated within the cavity apart from each other and fixedly attached to the body portion; a rotor may include an output shaft which extends through the first and second bearings and at least one magnet; and/or a stator casing having at least one electromagnet configured to generate an magnetic field to interact with a magnetic field of the at least one magnet to reciprocally drive the rotor and stator casing linearly and rotationally relative to the body portion and out of phase with each other so as to dampen vibration.

The personal care apparatus may further include first and second biasing members each of which may be situated between the stator casing and one of the first and second bearings. It is also envisioned that the first and second biasing members may be configured to linearly and rotationally bias the stator relative to the body. The personal car apparatus may further include a controller which may generate at least one drive signal to drive the at least one electromagnet at a resonant frequency of the stator casing. The personal care apparatus may further include a workpiece having a brush head coupled to one of the opposed ends of the output shaft.

The present invention is explained in further detail in the following exemplary embodiments and with reference to the figures, where identical or similar elements are partly indicated by the same or similar reference numerals, and the features of various exemplary embodiments being combinable. In the drawings:

FIG. 1 shows a side view of a portion of an electromagnetic motor arrangement (EMA) in accordance with embodiments of the present system;

FIG. 2 shows the EMA mounted within a personal care apparatus in accordance with embodiments of the present system;

FIG. 9 shows a detailed partially cutaway front perspective view of a portion of an EMA 900 in accordance with embodiments of the present system.

Figure 3:
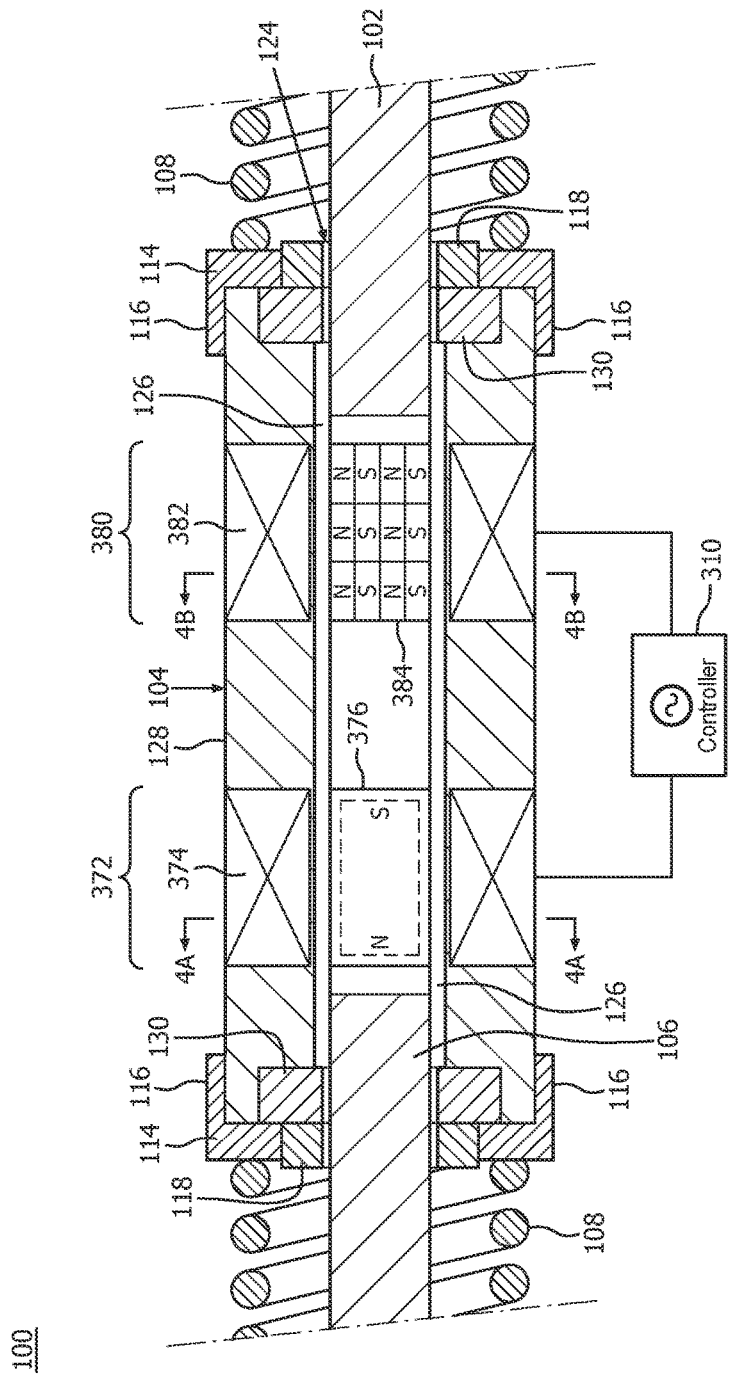
FIG. 3 shows a detailed cross sectional view of a portion of the EMA of FIG. 1 in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

FIG. 1 shows a side view of a portion of an electromagnetic motor arrangement (EMA) 100 in accordance with embodiments of the present system. The EMA 100 may include one or more of a stator 104, a rotor 106, biasing members 108, and bearings 110.

The rotor 106 may include at least one magnet and a shaft 102 (e.g., an output or drive shaft) having opposed ends 122, the shaft 102 may extend through openings 112 in the bearings 110 which may be lined with a suitable bearing material so as to reduce friction between a surface of the corresponding bearing 110 and the shaft 102 and may provide for shaft to reciprocate radially and/or longitudinally relative to a longitudinal axis LA of the shaft 102 as illustrated by arrows 101 and 103, respectively. Accordingly, the rotor 106 may reciprocate radially and/or longitudinally relative to the bearings 110. However, in yet other embodiments, it is envisioned that the bearings 110 may include plain bearings (e.g., a friction reducing surface, etc.), liquid bearings, ball bearings and/or the like for friction reduction between the bearings 110 and the shaft 102. The bearings may be configured to support loading of the shaft 102 during use such as loading due to forces generated by the EMA 100 and a user (e.g., transferred via a brush head coupled to the shaft 102 of the rotor 108). The shaft 102 may include a single piece or a two piece shaft. For example, in some embodiments, the rotor may include a center section including at least one magnet and at least one shaft which extends through the center section.

The rotor 108 may include one or more magnets such as permanent magnets which may interact with magnetic (e.g., electro-magnetic) fields generated by at least one electromagnet of the stator 104 operating under the control of a controller. These magnetic fields may provide a magnetic force which may cause the shaft to move linearly and/or radially relative to the longitudinal axis LA of the shaft 102 as shown by arrows 105 and 103, respectively. The shaft 102 may extend through the openings 112 of the bearings 110, the biasing members 108, and a cavity 126 of the stator 104. Further, the at least one of the bearings 110, the biasing members 108, and the stator 104 may be situated between the opposed ends 122 of the shaft 102.

The stator 104 may include a center portion 128 which may include the at least one electromagnet, controlled by the controller and suitable to generate a magnetic field or fields suitable for interacting with the magnetic field or fields of the at least one magnet of the rotor to reciprocally drive the rotor and the stator casing linearly and rotationally out of phase with each other. The stator 104 may include one or more weights for adjusting a weight and/or moment of inertia of the stator 104. The stator 104 may be situated between the bearings 110 and may be biased in position radially (rotationally) and/or linearly relative to a longitudinal axis of the stator 104 (which in the present embodiments may correspond with LA for the sake of clarity) by the biasing members 108 (which are positioned between the stator 104 and an adjacent bearing 110). The biasing members 108 may be similar to each other (e.g., may have the same or substantially same spring constant k) so that the stator 104 may be equally biased between to the bearings 110. However, in yet other embodiments, the spring constants k of the biasing members 108 may differ from each other.

In accordance with some embodiments, the stator 104 and/or rotor 108 may include weights which may be used to adjust inertia and/or mass of the stator 104 and/or rotor 108 to tune a ratio of inertia in an axial and/or rotational sense, in such a way that it matches a ratio of spring stiffness in the axial (e.g., linear) and/or rotational direction. The weights may be integrally formed with the stator 104 and/or rotor 108, if desired. For example, in accordance with some embodiments, thickness and/or types of materials may be selected so that a desired weight may be obtained. However, in yet other embodiments, it is envisioned that the weights may be attached to stator 104 and/or rotor 108, if desired. For example, in accordance with some embodiments, an end cap 114 may include a washer may be attached to a side thereof such that the washer is situated between an end of the end cap 114 and an adjacent washer and the shaft passes through a central opening of the washer. In accordance with yet other embodiments, material may be removed from one or more of the stator 104 and rotor 108 so as to attain a desired weight and/or moment or inertia.

The end caps 114 may include tabs 116 which may extend about an outer periphery of a center portion 128 of the stator 104 so as to positively locate the end caps 114 relative to the stator 104. The end caps 114 may include bearings 118 having openings 124 through which the shaft 102 may pass and which may support the stator 104 relative to the shaft 102. Accordingly, the stator 104 may be supported by rotor 106. The bearings 118 may reduce friction between a surface of the corresponding bearing 118 and the shaft 102 so that the rotor 106 may reciprocate radially and/or longitudinally relative to the stator 104. In some embodiments, it is envisioned that the bearings 118 may include plain bearings (e.g., a friction reducing surface, etc.), liquid bearings, ball bearings and/or the like for friction reduction between the bearings 118 and the shaft 102 so that the rotor 106 (and its shaft 102) and the stator 104 may move freely (e.g., along or about the LA) relative to each other and/or the bearings 110 during operation of the EMA 100.

The rotor 106 may have a preference axial position due to a magnetic setup of the EMA 100. For example, iron cores of the EMA 100 may be biased (e.g., by magnetic forces of permanent magnets of the EMA 100) so that they are aligned to the middle of adjacent permanent magnets, This may be known as a preference position of the rotor 106 relative to the stator 104. The biasing members 108 (e.g., coil springs) on each side of the stator 104 may further bias the stator 104 in a preference position (e.g., axially and rotationally). Accordingly, when not in use (e.g., when off), magnetic forces due to permanent magnets of the EMA 100 may bias to rotor 106 and stator 104 into an off position or preference position.

FIG. 2 shows the EMA 100 mounted within a personal care apparatus (PCD) 200 in accordance with embodiments of the present system. The personal care apparatus 200 may include an automatic toothbrush 256 having a body 242 with a handle 258 at least one wall 260 which defines at least part of a cavity 248 in which the EMA 100 may be situated. More particularly, the bearings 110 may be coupled to the body 242 using any suitable method such as friction fits, adhesives, tabs, retaining rings, screws, etc. The position of the bearings 110 may be such that the biasing members 108 have a desired preload.

The shaft 102 may be coupled to an extension 240 which may extend between the shaft 102 and a workpiece 242 such as a brush head having a plurality of bristles 246 situated at one end of the workpiece 242. The extension 240 may extend through an opening 244 in the body 242. The handle portion 258 may be configured to be grasped by a user.

The PCD 200 may further include a controller 250, a power storage device 252 such as a battery and/or capacitor, and an optional inductive charger 254. The inductive charger 254 may include at least one coil which may generate an induced signal when exposed to an external electromagnetic field and may provide this induced signal to the controller 250 coupled thereto. The controller 250 may then process the input induced signal and store the processed induced signal in the power storage device 252 for later use. The controller 250 may be coupled to one or more electromagnets of the EMA 100 which may provide an electromagnetic force to reciprocally drive the shaft 102 linearly and/or rotationally. The controller 250 may generate and provide a drive signal to each of these one or more electromagnets to generate a corresponding magnetic field. Each drive signal may have a desired frequency, voltage, and amplitude which may be determined by the controller 250. The controller 250 may form the drive signal to include a desired type of signal such as a sinusoidal signal (e.g., an alternating current (AC) signal), a pulse-width modulated signal (PWM), etc., as may be desired. Thus, the controller 250 may drive the electromagnets of the EMA 100 at a desired frequency, waveform, and/or duty cycle. An on/off switch may be provided to signal the controller 250 to turn the EMA 100 on or off and may, for example be mounted on a surface of the body 242 such as on a surface 248 of the handle 258, if desired.

FIG. 3 shows a detailed cross sectional view of a portion of the EMA 100 of FIG. 1 in accordance with embodiments of the present system. At least one electromagnet may include a linear electromagnet assembly 372 and a rotational electromagnet assembly 380. The linear electromagnet assembly 372 may include at least one electromagnet such as electromagnet 374 which may generate a magnetic field (e.g., a first electromagnetic field) which may interact with a magnetic field of at least one magnet 376 of the rotor 106 so as to cause the rotor 106 (and the shaft 102 attached thereto) to be linearly attracted or repelled by this interaction dependent upon a polarity of the first magnetic field. However, as both the stator 104 and the rotor 106 are free to move linearly relative to each other, they will reciprocate relative to each other about 180 degrees out of phase. Similarly, the rotational electromagnet assembly 380 may include at least electromagnet, such as electromagnet 382 which may generate a magnetic field (e.g., a second electromagnetic field) which may interact with magnetic field of another at least one magnet 384 of the rotor 106 so as to cause the rotor 106 to be rotationally attracted or repelled by this interaction depending upon a polarity of the second magnetic field. However, as both the stator 104 and the rotor 106 are free to move rotatably relative to each other, they will rotatably reciprocate relative to each other about 180 degrees out of phase.

The controller 310 may drive the electromagnet(s) of the EMA 100 such as the electromagnet 374 and/or the electromagnet 382. Accordingly, the controller 310 may generate and output at least one drive signal to drive the electromagnets 374, 382 of the EMA 100. For example, the controller may generate a first drive signal (DRV1) which may be provided to the electromagnet 374 and may generate a second drive signal (DRV2) and provide this drive signal to the electromagnet 382 so as to drive the electromagnets 374 and 382, respectively, so that they output a magnetic field in accordance with their respective drive signals. In some embodiments the first and second drive signals may be the same as or different from each other in one or more of amplitude, frequency, waveform, and/or duty cycle. However, for the sake of clarity, it will be assumed that the first and second drive signals are the same as each other and include a sinusoidal waveform (e.g., an alternating current (AC) waveform) having a frequency which corresponds with a linear and rotational resonance frequencies of the stator 104 and rotor 106. In yet other embodiments, it is envisioned that the drive signal may include a pulse-widthmodulated (PWM) signal having a desired, duty factor, phase, form (e.g., shape such as sinusoidal, square wave, etc.), and/or frequency. In accordance with some embodiments, the controller 310 may provide at least one drive signal to at least one of the electromagnets 374 and 382 using any suitable coupling such as a wired coupling.

The controller 310 may be coupled to the electromagnets 374 and 382 using any suitable conductor such as a ribbon, a cable, a slip ring, wireless circuit, etc. It is further envisioned that in some embodiments the biasing members 108 may be electrically isolated from each other and may couple the controller 310 to the first and/or second electromagnets 374 and 382, respectively, if desired.

The rotor 106 may have linear and rotational resonant frequencies and the stator 104 may have linear and rotational resonant frequencies. The linear and resonant frequencies of the shaft 102 and the stator 104 may correspond with each other. Accordingly, both the rotor and stator may resonate in the system substantially at about the same linear and/or rotational frequencies. Then, when driven by the actuators at their resonant frequencies, the shaft 102 and the stator 104 may reciprocate linearly and rotationally near or substantially at their resonant frequencies and form a resonant system driven at the driven frequency. In accordance with some embodiments, the drive signal may have a frequency that is slightly different from (e.g., substantially at (e.g., a threshold value away from a corresponding resonant frequency as may be desired) but not equal to one or more of the resonant frequencies to assure system stability.

When driven for example, at their linear and/or rotational resonant frequencies (e.g., using an AC drive signal or signals generated by the controller 310), the stator 104 reciprocates linearly and rotationally in opposite phase (e.g., 180 degrees out of phase) to the rotor 106 which acts as a rotational and linear balance weight to dampen rotational and linear vibration, respectively.

Figure 4A:
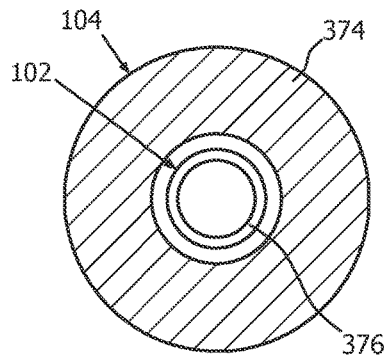
FIG. 4A shows a cross-sectional side view of a portion of a toothbrush system taken along lines 4A-4A of FIG. 3 in accordance with embodiments of the present system.
Figure 4B:
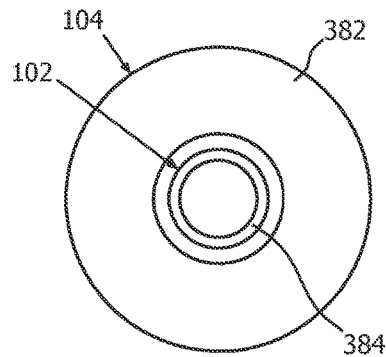
FIG. 4B shows a cross-sectional side view of a portion of a toothbrush system taken along lines 4B-4B of FIG. 3 in accordance with embodiments of the present system.

FIG. 4A shows a cross-sectional side view of a portion of a toothbrush system 100 taken along lines 4A-4A of FIG. 3 in accordance with embodiments of the present system; and FIG. 4B shows a cross-sectional side view of a portion of a toothbrush system 100 taken along lines 4B-4B of FIG. 3 in accordance with embodiments of the present system.

Rotational or linear electromagnetic motor arrangement (EMA) will now be described with reference to FIGS. 6 through 9. Each of these motors may be of a type (e.g., linear or rotational) which provides reciprocating linear or rotational output, respectively, at the output shaft. However, if both linear and rotational output at the output shaft is desired, two or more of these EMAs of different types may be coupled to the same output shaft. For example, a linear-type EMA may be coupled to an output shaft of a rotational-type EMA and when both the linear- and rotational-type EMAs are driven by the controller, the output shaft may provide reciprocating linear and rotational output. Accordingly, the linear and rotational EMAs may be situated along the output shaft in a serial manner.

Figure 6:
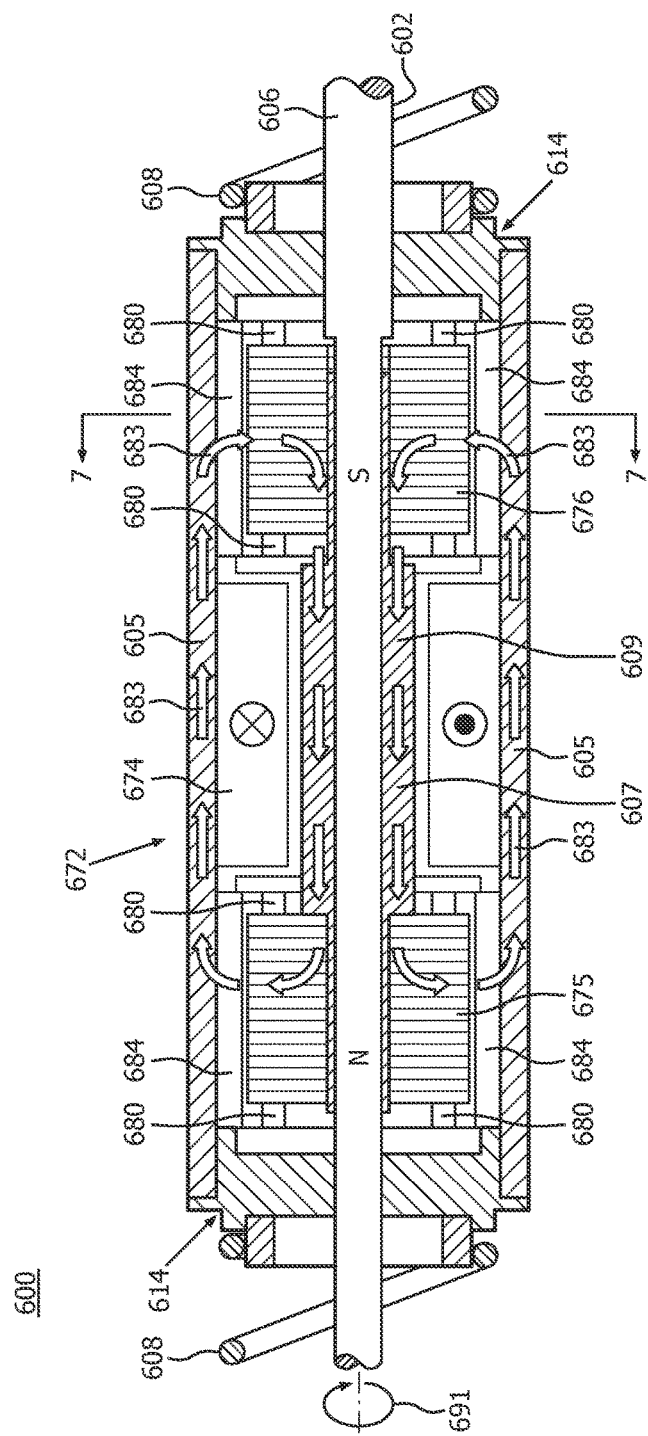
FIG. 6 shows a detailed cross-sectional view of a portion of an EMA 600 using a single electromagnet in accordance with embodiments of the present system.

FIG. 6 shows a detailed cross-sectional view of a portion of an EMA 600 using a single electromagnet in accordance with embodiments of the present system. The EMA 600 may be similar to the EMA 100 and may include a stator 604, a rotor 606, end caps 614, and biasing members 608, which are respectively similar to the stator 104, a rotor 106, end caps 114, and biasing members 108 of the EMA 100. However, rather than using dual actuator assemblies (e.g., linear and rotary) as may be used by the EMA 100, the EMA 600 may include a single coil assembly 672 for rotational motion. Further, the caps 614, may include internal bearings for slidably and/or rotatably supporting the stator 604 relative to the rotor 606. The coil assembly 672 may include at least one coil 674 which may generate an electromagnetic field to drive at least the rotor 606 and the stator 604 in opposite directions rotationally from each other as will be discussed below. More particularly, end portions 675 and 676 may be electromagnets which may take on a magnetic polarity when immersed in the electromagnetic field generated by the at least one coil 674.

The rotor 606 may include a shaft 602 having a core portion 607 with a high permeability to guide a magnetic field in a desired direction which is fixedly attached to the shaft 602. The core portion 607 may include a center portion 609 and the end portions 675 and 676. The end portions 675 and 676 may be situated on opposite sides of the at least one coil 674.

Similarly to the rotor 606, the stator 604 may have core area of high permeability to guide the electromagnetic field. For example, the core area of the stator 604 may include a shell 605 area and/or optional spacers 684 which may prevent portions of adjacent components from touching each other during, for example, assembly, etc. Further, the rotor may include permanent magnets such as magnets 680 which may have polarities as shown.

The cores of the rotor 606 and the stator 604 may interact with or otherwise guide the magnetic field so as to be rotationally attracted or repelled from each other so as to move out of phase with each other. The attraction and/or repulsion may depend upon a polarity (e.g., direction) of the magnetic field. As both the stator 604 and the rotor 606 are free to move linearly relative to each other, attraction and repulsion forces generated an alternating magnetic field direction will cause both the stator 604 and the rotor 606 to reciprocate rotationally relative to each other about 180 degrees out of phase.

The at least one coil 674 may be driven by a controller of the system using any suitable drive signal such as the discussed elsewhere. The controller may be coupled to the at least one coil 674 using any suitable conductor such as a ribbon, a cable, a slip ring, etc. However, in yet other embodiments, it is envisioned that the biasing members 608 may be electrically isolated from each other and may couple the controller to the at least one coil 674, if desired. In yet other embodiments it is envisioned that the controller may be coupled to the at least one coil 674 using any suitable coupling method.

Figure 7:
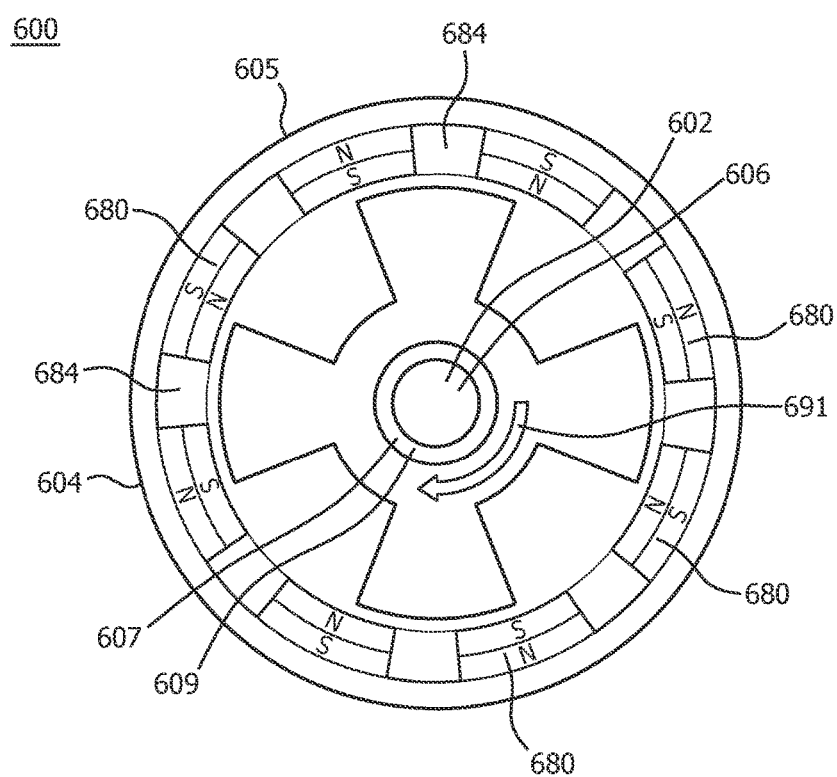
FIG. 7 shows a cross-sectional side view of a portion of the EMA taken along lines 7-7 of FIG. 6 in accordance with embodiments of the present system.

FIG. 7 shows a cross-sectional side view of a portion of the EMA 600 taken along lines 7-7 of FIG. 6 in accordance with embodiments of the present system. The magnetic field generated by the at least one coil 674 may be guided by the core portions of the rotor 606 and the stator 604 in a desired direction as shown by arrows 683 (when driven by a current in a first direction as shown in FIG. 6) which may result in a forces (as in the direction of arrow 691) which may cause the rotor 606 to move rotationally in the direction of arrow 691 while the stator 604 may move rotationally in the opposite direction.

With reference to FIGS. 6 and 7, in FIG. 6 the arrows 683 illustrate magnetic flux for a primary loop (shown as a figure eight-type loop when viewed using a planar view). Further, the rotor and/or the stator 604 may include permanent magnets to form other magnetic fields, if desired.

Figure 8:
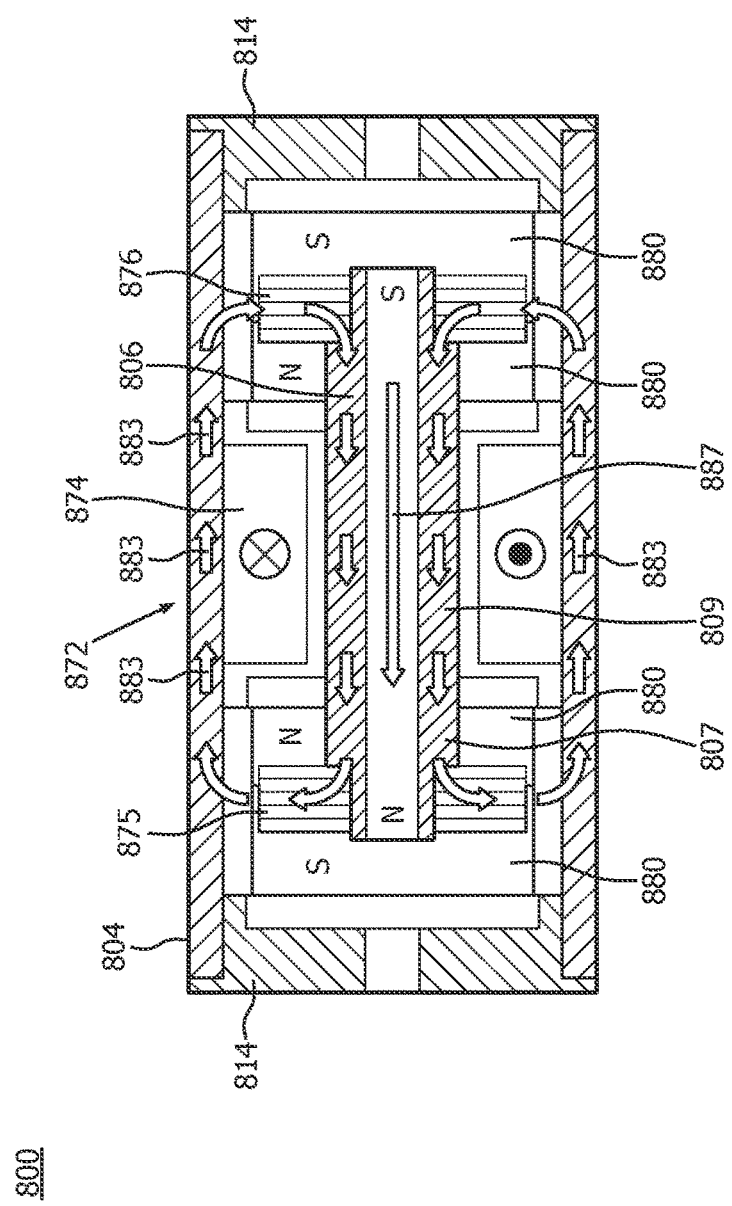
FIG. 8 shows a detailed cross-sectional view of a portion of an EMA using a single electromagnet in accordance with embodiments of the present system.

FIG. 8 shows a detailed cross-sectional view of a portion of an EMA 800 using a single electromagnet in accordance with embodiments of the present system. The EMA 800 may be similar to the EMA 600 and may include a stator 804, a rotor 806, end caps 814, and biasing members, which are respectively similar to the stator 604, a rotor 606, end caps 614, and biasing members 608 of the EMA 600. However, the stator 804 may have a different permanent magnet arrangement 880 than that of the stator 604. For example, the permanent magnets 880 may be arranged with the polarities as shown. A coil assembly 872 may include at least one coil 874 which may generate an electromagnetic field (e.g., see arrows 883) to drive at least the rotor 806 and the stator 804 linearly in opposite directions from each other as will be discussed below. For example, when the electromagnetic field is in the direction of arrows 883, a force (as shown by arrow 887) may drive the rotor 806 in the corresponding direction. The rotor 806 may include a shaft having a core portion 807 with a high permeability to guide a magnetic field in a desired direction which is fixedly attached to the shaft. The core portion 807 may include a center portion 809 and electromagnets 875 and 876. The electromagnets 875 and 876 may be situated on opposite sides of the at least one coil 874 The shaft portion of the rotor 806 is not shown for the sake of clarity. The EMA 800 may be substantially symmetric radially.

FIG. 9 shows a detailed partially cutaway front perspective view of a portion of an EMA 900 in accordance with embodiments of the present system. The EMA 900 may be similar to the EMA 600 and may include a stator 904, a rotor 906, end caps 914, at least one coil 972, and biasing members 908, which are respectively similar to the stator 604, a rotor 606, end caps 614, at least one coil 672, and biasing members 608 of the EMA 600. However, EMA 900 may have a different permanent magnet arrangement than that of the EMA 600. For example, rotor 906 may include permanent magnet configurations 981 fixedly attached to the rotor 906 and stated on opposite sides of an at least one coil 972.

Each of the permanent magnet configurations 981 may include a plurality of radially-disposed permanent magnets 980. Further, the stator 904 may include electromagnets 984 having a high permeability and situated on opposite sides of the at least one coil 972 to guide a magnetic field generated by the electromagnets 984 in a desired direction such as shown by arrows 983. Laminations may be provide to reduce Eddy currents and, thus, reduce energy losses during use. During operation, the coil 974 may generate the electromagnetic field (e.g., see arrows 983) to drive at least the rotor 906 and the stator 904 linearly in opposite directions from each other as will be discussed below. The rotor 906 may include a shaft 902 having a core portion 907 with a high permeability to guide the magnetic field in a desired direction and which may be fixedly attached to the shaft 902. Further, the core portion 907 may include a center portion 909.

During use, primary and secondary magnetic loops may be established in the EMA 900. The primary magnetic field may be illustrated by loops formed by the arrows 983 and the secondary magnetic field may be illustrated by arrows 985 as shown. The primary loops may provide linkage flux (related to torque) and a magnetic spring (e.g., in the forward direction). The secondary loops may function to provide a magnetic spring (e.g., in the reverse (e.g., counter) direction). Thus, the large loop may generally provide torque and the small loops may generally provide stiffness.

Thus, embodiments of the present system provide a resonant motor such as an EMA that includes an inner rotor (formed by the rotor 106) and an outer stator (e.g., the stator 104) in which the motor (e.g., the EMA 100) is configured such that both the inner rotor and outer stator are capable of motion out-of-phase with each other; cancelling or reducing vibration transferred to the user. Grounded bearings may be provided to support the rotor and bearings between the rotor and the stator of the motor. The outer stator is configured to translate both axially and rotationally though a small range of motion and the stator may be attached to ground (e.g., a body) via a biasing member such as a spring (e.g., a coil spring or the like). However, in yet other embodiments, it is envisioned that the biasing member may include any suitable biasing member such as an elastic (e.g., plastic) member. Similarly, the inner rotor is configured to translate both axially and rotationally though a small range of motion relative to the outer stator. The inner rotor and the outer stator are both configured to translate both axially and rotationally though a small range of motion relative to the ground and out of phase with each other (e.g., the inner rotor and the outer stator). The outer stator may include at least one electromagnet configured to interact with a magnetic field of a magnet of the inner rotor so as to cause the inner rotor and outer stator to be linearly and rotationally attracted or repelled by the magnetic field depending upon the polarity of the magnetic field. A controller may be provided to drive the electromagnet(s) with at least one drive signal (DRV) so that polarities of the magnetic fields generated by the electromagnet alternates so as to reciprocally linearly and rotationally drive the inner rotor and outer stator out of phase (e.g., 180 degrees out-of-phase) with each other. This out of phase reciprocal and linear motion between the outer stator and inner rotor will act to dampen or otherwise attenuate vibration so as to prevent vibration of the handle of the body portion which may cause user discomfort.

In yet other embodiments, a personal care apparatus may be provided which may include at least one of a toothbrush and flosser.

It is further envisioned that in yet other embodiments, the EMA may be configured as desired and sized in accordance with an expected load. For example, EMAs for a child's toothbrush may have a similar shape but have a smaller size than does an EMA of an adult's toothbrush. Further, in yet other embodiments, the EMA may have its own housing and may be assembled within this housing. Accordingly, an assembled EMA (e.g., an EMA cartridge) may be inserted as an integrated unit into an outer housing of a toothbrush to ease assembly. A controller may be provided and may be integrated with the assembled EMA (e.g., the EMA cartridge) or may be separate from the assembled EMA and attached to the assembled EMA during installation within the outer housing of the toothbrush.

It is further envisioned that in embodiments of the present system, the inner rotor may include an output shaft such as a drive shaft. The inner rotor may be mounted upon bearings which are mechanically grounded to the outer housing (e.g., body portion) of the toothbrush (or to the housing of the EMA when using an EMA cartridge). This may locate a linear axis (e.g., see LA) of the motor relative to the outer housing of the toothbrush. Further, the bearings may be configured to support the inner rotor so that the inner rotor maintains a desired general position and/or orientation relative to the outer housing of the toothbrush during use.

Biasing members such as springs may be provided and coupled to a ground (e.g., stationary portion of the toothbrush body) on one side and coupled to the outer stator on the other and may act to bias the outer stator in a desired position and/or orientation relative to the outer housing of the toothbrush. Accordingly, the outer stator to be displaced linear and rotationally (e.g. angularly) relative to the outer housing of the toothbrush and may be biased back to a neutral bias position (both radially and linearly) absent any forces applied to the outer stator. When the toothbrush is operated (when power is applied to the EMA), the outer stator and inner rotor will both translate and rotate relative to the outer housing of the toothbrush, and the outer stator and the inner rotor will move out-of-phase with each other both linearly and rotationally which may attenuate or otherwise dampen vibration.

A workpiece assembly may be removably attached to the inner rotor and may include a plurality of bristles or other elements (e.g., scrapers, etc.) which may form a brush head. One or more electromagnets may be provided to drive the inner rotor both linearly and rotationally (e.g. angularly) relative to the outer housing of the toothbrush with sufficient motion and force such that during operation with the toothbrush will provide adequate efficacy for the intended use (e.g., plaque removal). Similarly, during use, the electromagnets may drive the outer stator both linearly and rotationally (e.g. angularly) relative to the inner rotor to dampen or otherwise attenuate vibration. This active vibration dampening (e.g., vibration reduction) may reduce vibration sensed by the user during use so as to increase user convenience. Thus, during use (assuming the workpiece is attached to the inner rotor) the inner rotor will move sufficiently to provide adequate efficacy (plaque removal) while the outer stator will move sufficiently to cancel vibratory forces (rotational and/or linear). The spring allows the stator to move in counterphase to the rotor, cancelling most of the acceleration forces initiated by the moving rotor. The transmitted acceleration forces to the housing are determined by the movement of the stator and the spring stiffness. The ratio of stator to rotor movement is determined by the mass/inertia ratio. The actual force to the housing then is movement times stiffness of the connection (the springs). The force to the housing with the mass/inertia of the housing result in movement of the housing which is felt as vibration. A very stiff spring will not allow the stator to move sufficiently, so vibration cancellation is low, a very weak spring will work well for vibration cancellation, but will reduce performance of the rotor under load.

Further, in accordance with some embodiments of the present system, an electrical lead such as a ribbon, a wire, a group of wires, etc., may be included to provide electrical power to the outer stator (e.g., to at least one electromagnet of the outer rotor). For example, in accordance with some embodiments, this electrical lead may be coupled between the controller and the outer stator to provide power from the controller to the outer stator (e.g., to at least one stator of the solenoid). However, in yet other embodiments, it is envisioned that the biasing members may be conductive and provide electrical power to the outer stator. For example, it is envisioned that in some embodiments the biasing members may be electrically isolated from each other and electronically coupled to the outer stator so as to provide electrical power to at least one electromagnet of the outer stator. Further, in yet other embodiments, it is envisioned that the outer stator may include one or more permanent magnets and/or laminated portions.

Figure 5:
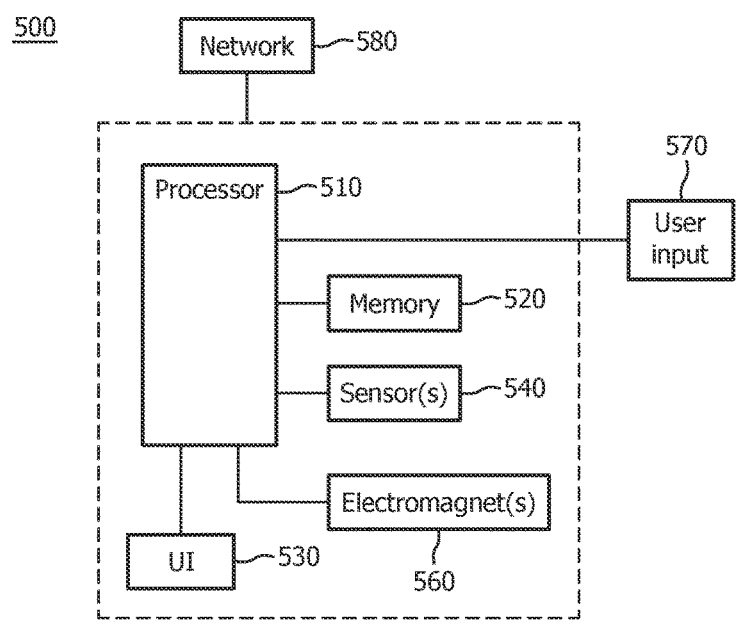
FIG. 5 shows a portion of a system in accordance with embodiments of the present system.

FIG. 5 shows a portion of a system 500 in accordance with embodiments of the present system. For example, a portion of the present system 500 may include a processor 510 (e.g., a controller) operationally coupled to a memory 520, a user interface (UI) 530, sensors 540, electromagnets 560, and a user input portion 570. The memory 520 may be any type of device for storing application data as well as other data related to the described operation. The application data and other data are received by the processor 510 for configuring (e.g., programming) the processor 510 to perform operation acts in accordance with the present system. The processor 510 so configured becomes a special purpose machine particularly suited for performing in accordance with embodiments of the present system.

The operation acts may include configuring the system 500 by, for example, configuring the processor 510 to obtain information from user inputs such as from the user input portion 570 and/or the memory 520 and processing this information in accordance with embodiments of the present system to determine a corresponding output signal (e.g., a drive signal) to drive the electromagnets 560. The user input portion 570 may include a switch such as an on/off switch and/or function selection switches (e.g., to select cleaning modes), a keyboard, a mouse, a trackball and/or other device, including touch-sensitive displays, which may be stand alone or be a part of a system, such as part of an OHD, a personal computer, a notebook computer, a netbook, a tablet, a smart phone, a personal digital assistant (PDA), a mobile phone, and/or other device for communicating with the processor 510 via any operable link. The user input portion 570 may be operable for interacting with the processor 510 including enabling interaction within the UI as described herein. Clearly the processor 510, the memory 520, the UI 530 and/or user input portion 570 may all or partly be a portion of a computer system or other device such as a client and/or server as described herein.

The processor 510 may render the information that it generates such as a battery charge level, battery charge required, operating mode (e.g., charging, operating, error, etc.), etc., on the UI 530 such as on a display of the system (e.g., graphics capable display, light emitting diodes (LEDs), a liquid crystal display (LCD), etc.

The methods of the present system are particularly suited to be carried out by processor programmed by a computer software program, such program containing modules corresponding to one or more of the individual steps or acts described and/or envisioned by the present system.

The processor 510 is operable for providing control signals and/or performing operations in response to input signals from the user input portion 570 as well as in response to other devices of the network 580 and executing instructions stored in the memory 520. For example, the processors 510 may obtain feedback information from the sensors 540 and may process this information to determine operating modes. For example, when the sensors 540 indicate that an inductive charging coil is providing an inductive charge, the processor 510 may enable a battery charging mode to charge one or more power storage devices (e.g., batteries, capacitors) of the system 500, if desired. The processor 510 may include one or more of a microprocessor, an application-specific or general-use integrated circuit(s), a logic device, etc. Further, the processor 510 may be a dedicated processor for performing in accordance with the present system or may be a general-purpose processor wherein only one of many functions operates for performing in accordance with the present system. The processor 510 may operate utilizing a program portion, multiple program segments, or may be a hardware device utilizing a dedicated or multi-purpose integrated circuit.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

The invention claimed is:

1. A personal care apparatus with active vibration dampening, comprising:
  a body having at least one wall) and an opening, wherein the at least one wall defines at least a part of a cavity;
  first and second bearings situated apart from each other within the cavity, the first and second bearings being fixedly coupled to the body within the cavity;
  an outer stator that comprises a stator casing movably coupled within the cavity, the outer stator being configured to translate both axially and rotationally through a range of motion relative to the body; and
  an inner rotor that comprises a rotor situated partly within the stator casing, the inner rotor being configured to translate both axially and rotationally through a range of motion relative to the outer stator, wherein the rotor comprises an output shaft and a section that includes at least one magnet, wherein the output shaft extends (i) through the section, (ii) through a cavity of the stator casing, and (iii) through openings in the first and second bearings,
  wherein the stator casing further comprises a portion having at least one electromagnet configured to generate a magnetic field to interact with a magnetic field of the at least one magnet of the rotor to (i) reciprocally drive both the inner rotor and outer stator linearly and rotationally relative to the body and (ii) move the inner rotor and outer stator out of phase with each other both linearly and rotationally so as to dampen vibration of the body.

2. The apparatus of claim 1, further comprising first and second biasing members, wherein the stator casing is movably coupled to the body within the cavity via the first and second biasing members disposed between opposite ends of the stator casing and a respective one of the first and second bearings, wherein the output shaft further extends (i) through the section, (ii) through the cavity of the stator casing, (iii) through the first and second biasing members, and (iv) through openings in the first and second bearings.

3. The apparatus of claim 2, wherein the first and second biasing members linearly and rotationally bias the stator relative to the body.

4. The apparatus of claim 1, further comprising a controller configured to generate at least one drive signal to drive the at least one electromagnet substantially at a resonant frequency of a spring-mass system of the stator casing and rotor.

5. The apparatus of claim 1, further comprising a workpiece having a brush head of bristles coupled to one end of the output shaft.

6. The apparatus of claim 1, wherein the stator casing is supported by the output shaft of the rotor extending through openings in end caps of the stator casing.

* * * * *